United States Patent [19]

Cannell

[11] 4,059,644
[45] Nov. 22, 1977

[54] HIGH DENSITY FUELS

[75] Inventor: Lawrence G. Cannell, Houston, Tex.

[73] Assignee: Shell Oil Company, Houston, Tex.

[21] Appl. No.: 657,413

[22] Filed: Feb. 12, 1976

[51] Int. Cl.$^2$ .................. C07C 13/00; C07C 13/28
[52] U.S. Cl. .......................... 260/666 PY; 260/683.9;
   44/80; 149/109.4; 149/120
[58] Field of Search ............ 260/666 PY, 683.9;
   44/80; 149/109.4, 120

[56] References Cited
U.S. PATENT DOCUMENTS 3,002,829  10/1961  Kolfenbach et al. ............ 260/683.9

Primary Examiner—Veronica O'Keefe
Attorney, Agent, or Firm—Ronald R. Reper

[57] ABSTRACT

A process for making high density fuels by heating a mixture of cyclopentadiene dimer and methylcyclopentadiene dimer at a temperature sufficient to promote substantial formation of the Diels-Alder trimer of the monomeric cyclopentadienes, followed by hydrogen saturation of the olefinically unsaturated trimerization product.

7 Claims, No Drawings

HIGH DENSITY FUELS

BACKGROUND OF THE INVENTION

This invention relates to the production of high density fuels by oligomerization of a mixture of cyclopentadiene dimer and methylcyclopentadiene dimer to their co-trimer followed by hydrogenation of the oligomerization product.

High density fuels are desirable to provide a high energy fuel source while at the same time minimizing the volume that the fuel occupies. Such fuels are important, for example, as fuels for certain military jet aircraft which have limited fuel storage capability. High density fuels permit maximizing the range of these aircraft by providing high energy per unit of volume occupied by the fuel.

To perform satisfactorily in such applications, the fuels must satisfy certain physical property requirements. The fuels must remain in liquid state at the low temperature experienced by aircraft flying at high altitude. This generally means that the fuel must have a melting point no greater than, if not substantially below $-20°$ C. To provide high energy per unit volume, it is generally desired that the fuels have a liquid density approaching or exceeding 1.0 gm/ml as compared to 0.75–0.8 gm/ml for kerosene. Liquid hydrocarbon fuels of this density necessarily contain multiple fused small rings, i.e., fused cyclic $C_3$, $C_4$ and $C_5$ rings. However, most multiple ring compounds with a density of about 1.0 gm/ml have unacceptably high melting points. For example, the most common cyclopentadiene dimer has a melting point of $32°$ C and its hydrogenated derivative has a melting point of $77°$ C.

A few satisfactory compounds are known and have been utilized for these volume critical services. For example, U.S. Pat. No. 3,377,398 discloses a method for dimerizing bicyclo(2.2.1)hepta-2,5-diene over an iron complex catalyst. However, bicycloheptadiene must first be synthesized, generally by reaction between cyclopentadiene and acetylene. U.S. Pat. No. 3,381,046 discloses a process whereby a specific exo-stereo isomer of cyclopentadiene dimer and methylcyclopentadiene dimer is produced from and then isolated from the endo-isomers of cyclopentadiene dimer and methylcyclopentadiene dimer. The complexity of these processes makes the product high density fuel expensive and has limited the broader usage of these fuels.

U.S. Pat. No. 3,002,829 discloses a simpler process for making high density fuel by dimerizing mixtures of cyclopentadiene, methylcylopentadine and dimethyl cyclopentadiene, topping off uncoverted monomer, followed by a two step hydrogenation of the product. This process is comparatively simple, but tetrahydro dimer mixture produced does not possess as high an energy content as the products of the more difficult syntheses above.

SUMMARY OF INVENTION

A simple process has now been discovered for making a high density fuel having a liquid density exceeding 1.0 gm/ml and a commensurately high heat of combustion which also has a suitably low melting point to permit its use of low temperatures. The high density fuel is produced by heating a mixture of cyclopentadiene dimer and methylcyclopentadiene dimer at a temperature of $150°–250°$ C for from 10 minutes to 3 hours in the substantial absence of oxygen. The reacting total trimer reaction product, which is primarily cyclopentadiene and methylcyclopentadiene co-trimer is completely hydrogenated by adding sufficient hydrogen to completely saturate the olefinically unsaturated bonds of the product, in the presence of hydrogenation catalyst at a temperature of from $25°–160°$ C and a hydrogen pressure of from 150–800 psia. Optionally, the co-trimer may be physically separated from the total trimer reaction product prior to hydrogenation of the co-trimer.

DESCRIPTION OF PREFERRED EMBODIMENTS

Suitable starting materials for production of the trimers of this invention are essentially pure cyclopentadiene, methylcyclopentadiene, cyclopentadiene dimer and methylcyclopentadiene dimer. These compounds are suitably obtained as separation products of conventional thermal cracking or pyrolysis of heavy naphthas, kerosenes, gas oils, or heavy distillates.

To take full advantage of the simplicity of the process it is preferred that only the cyclopentadiene dimer and methylcyclopentadiene be charged as feed. The molar ratio of cyclopentadiene dimer to methylcyclopentadiene dimer is suitably 3:1 to 1:3 and preferrably is from 1.5:1 to 1:1.5. When cyclopentadiene or methylcyclopentadiene monomers are provided as feed with their corresponding dimer, the molar ratio of combined monomers to dimer should preferably be about 2:1.

When only cyclopentadiene dimer and methylcyclopentadiene dimer are charged as feed, the mixture should be maintained at temperature of from $150°$ C to $250°$ C for a period of from 10 minutes to 3 hours in a closed reaction vessel. This temperature range is selected to effectuate sufficient dissociation of the dimer to the monomer, while at the same time the temperature is high enough for trimer formation from the dimer present and the monomer which has dissociated. By maintaining this temperature range the reaction rate for trimer formation exceeds the dissociation rate of the dimer to monomer and the trimer to dimer and monomer.

These competing reactions all take place simultaneously along with other reactions leading to formation of higher order oligomers. The time and temperature relationship must be considered to maximize the formation of trimer. A preferred temperature range is from $190°$ C to $230°$ C and a preferred time for the reaction is 15 minutes to 1 hour. The ability to charge only the dimer as feedstock to the process in order to produce timer by selection of the proper reaction temperature range is a major advantage of the process.

If cyclopentadiene and methylcyclopentadiene monomer are charged as feed along with cyclopentadiene dimer and methylcyclopendatiene dimer the reaction temperature utilized may be at the upper end of the temperature range utilized when only dimer is charged, viz., $175°–250°$ C and preferably $200°–250°$ C. In this situation, the time allowed may be less than the maximum allowed for only dimer feed, via., 10 minutes to 2 hours, and preferably 10–45 minutes, as a higher temperature favors trimerization as opposed to dimer dissociation and less time need be allowed for dimer dissociation to monomer.

The trimerization process may be conducted in a closed reaction vessel at the autogenous pressure of the reactants and product at the $150°–250°$ C temperature. It is highly desirable to minimize the amount of oxygen present in the reaction vessel to prevent formation of undesired oxidation products and gums. Generally this will mean that the oxygen present in the system will not exceed 0.1% wt of the reactant mixture present in the reaction vessel. Polymerization inhibitors and free radical inhibitors may optically be added. Suitable inhibitors include substituted phenols, for instance alkyl phenols, such as 2,6-di-tertiary-butyl-4-methyl phenol.

After the heating period, the product is then completely hydrogenated by adding a stoichiometric amount of hydrogen sufficient to saturate all olefinically unsaturated carbon bonds in the product. The hydrogenation is suitably conducted at a temperature of from 20°–160° C at a hydrogen pressure of 150–800 psig in the presence of a hydrogenation catalyst. The choice of temperature will depend upon the catalyst and pressure used. Group VIII catalysts are suitable hydrogenation catalysts, including platinum, palladium, rhodium, nickel and cobalt. Such catalysts may be supported or unsupported, with a supported catalyst being generally favored for commercial use. Suitable supports are charcoal, alumina, magnesia and the like. Preferred catalysts are supported nickel and cobalt. With such catalysts temperature of from 80°–120° C and hydrogen pressures of from 200–500 psig are preferred.

The cyclopentadiene and methylcyclopentadiene co-timer may optically be separated from the total trimer reaction product prior to hydrogenation by conventional physical separation techniques such as fractional distillation, vacuum distillation, fractional crystallization or extraction. Such separation may be desirable to permit reutilization of any unconverted monomer or dimer as feed to the process. Any such separation should be conducted in such a manner as to avoid exposure of the product to high temperatures which can cause dissociation of the trimer or further polymerization. Vacuum distillation is preferred in this regard.

The process of this invention is desirable because it is a simple two stage process, that uses feedstock, the cyclopentadiene and methylcyclopentadiene dimers, in the oligomer form in which it is readily available where produced in pyrolysis or thermal cracking plants.

The mixture of methycyclopentadiene dimer with the cyclopentadiene dimer is a unique feature that enables production of a co-trimer with acceptably low melting point. The choice of these starting materials enables, upon dissociation of the dimers to monomers the oligomerization of methylcyclopentadiene dimer with cyclopentadiene monomer, cyclopentadiene dimer with methylcyclopentadiene monomer, methylcyclopentadiene dimer with methylcyclopentadiene monomer, and cyclopentadiene dimer and cyclopentadiene monomer. The trimer reaction product is then a broad spectrum of methyl substituted, dimethyl substituted, trimethyl substituted, and non-methyl substituted trimers and isomers of each respective substituted trimer. This broad variety of compounds presumably prevents the mixture from easily forming a neat crystal lattice which in turn retards solidification upon cooling, and establishes the lower melting point for the product. Yet because of the fused ring structure, the composite trimer reaction product density exceeds 1.0 gm/ml. A comparison of the properties of the hydrogenated co-trimer that has been separated from the total hydrogenated trimer reaction product with the properties of competitive high density fuels is shown in Table I.

TABLE I

| Compound | Density, 20° C gm/ml | Melting Point ° C | Net Heat Of Combustion Btu/U.S. Gal. |
|---|---|---|---|
| Kerosene | 0.79 | — | 124,000 |
| tetrahydroderivative of cyclopentadiene dimer (exo isomer) | 0.9382 | −80 | 141,020 |
| tetrahydroderivative of methylcyclopentadiene dimer | 0.9235 | −30 | 141,160 |
| hydrogenated bicyclo(2.2.1)-hepta-2,5-diene dimer | 1.0925 | −30 to −60 | 162,500 |
| tetrahydroderivative of cyclopentadiene and methylcyclopentadiene co-trimers (hydrogenated co-trimer) | 1.02 | −30 | 154,000[a] |

[a]Estimated basis density and molecular structure

It can be seen from these data that the tetrahydrocyclopentadiene and methylcyclopentadiene co-trimer is competetive with any of these high density fuels in melting point and energy content. However, the process for production is much simpler and can be effected at a lower cost. Accordingly having lower cost, the co-timer may have broader commercial application than previous high density fuels and could conceivably be used in commercial aircraft, for example in supersonic aircraft where the fuel carrying ability and the maximum range cound be extended. The co-trimer of the co-trimer reaction product can either be used neat or mixed with other conventional or high density fuels.

The process may be further illustrated by way of the following example.

EXAMPLE I 0.8 Moles each of cyclopentadiene dimer (105 g of 3a,4,7,7a-tetrahydro-4,6-methanoindene) and methylcyclopentadiene dimer (128g) were heated in an autoclave at 230° C for 1 hour, and the resulting product was hydrogenated over 1%w Pt/carbon catalyst at a pressure 715 psig. The initial temperature was 80° C. The temperature was subsequently increased to 160° to ensure complete hydrogenation. Of the initial 233 g of feed, 218 g were recovered and 145 g of this was distilled after the Pt/carbon had been removed by filtration. Gas chormatographic analysis of the collected distillation fractions, when adjusted for the weight of the bottoms gave the following composition of the trimer reaction product:

$C_{10}$, trace
$C_{12}$, 19.5%w
trimers, 38.9% w
higher boiling, 32.2% w
bottoms, 9.4% w Thus about 100% of the cyclopentadiene dimer was converted to trimer or higher oligomers and 65.4% of the methylcyclopentadiene dimer was converted to trimer or higher oligomers for a 48% weight selectivity to trimer. The trimer was comprised of two principal fractions:

Cut 1 boiling point range 200°–220° C at a pressure of 5 mm of Hg

Cut 2 boiling point range 220°–253° C at a pressure of 5 mm of Hg

Cuts 1 and 2 were found to have a density of 1.014 gm/ml and 1.018 gm/ml, respectively, at 20° C. The density of the total product, including the $C_{12}$ dimer, the higher boiling fraction and the bottoms, before it had been distilled was 1.0292 gm/ml. Higher boiling as used here means that portion of the total reactor product boiling between 253° C and 300° C at a pressure of 5 mm of Hg. Cooling of a sample of the combined hydrogenated trimer (Cut 1 and Cut 2) showed that it became very viscous at −25° to −30° C.

What is claimed is:

1. A process for making high density fuel which comprises
   a. heating a mixture of cyclopentadiene dimer and methylcyclopentadiene dimer at a temperature of 150°–250° C for from 10 minutes to 3 hours provided that any oxygen present will not exceed 0.1%wt of the mixture, then
   b. hydrogenating the product of step (a) by reaction with sufficient hydrogen to completely saturate the olfinically unsaturated bonds of said product and in the presence of a hydrogenation catalyst at a temperature of from 25°–160° C and a hydrogen pressure of from 150–800 psig.

2. The process of claim 1 wherein the heating temperature employed in step (a) is between 190° C and 230° C and the heating time is from 15 minutes to 1 hour.

3. The process of claim 1 wherein the mixture contains cyclopentadiene dimer and methylcyclopentadiene dimer in a molar ratio of from 3:1 to 1:3.

4. The process of claim 1 wherein the hydrogenation is conducted at a temperature of from 80°–120° C at a hydrogen pressure of from 200 to 500 psig, in the presence of a Group VIII metal catalyst.

5. A process for making high density fuel which comprises
   a. heating a mixture of cyclopentadiene dimer and methyl cyclopentadiene dimer at a temperature of 150°–250° C for from 10 minutes to 3 hours provided that any oxygen present will not exceed 0.1%wt of the mixture, to form a co-trimer from said dimers, then
   b. separating said co-trimer from the unreacted dimers and higher order oligomers in the bulk reaction product,
   c. adding sufficient hydrogen to completely saturate the olefinically unsaturated bonds of the separated co-trimer in the presence of a hydrogenation catalyst at a temperature of from 25°–160° C and a hydrogen pressure of from 150–800 psig.

6. The process of claim 5 wherein said co-trimer is separated by a separation method selected from the class consisting of fractional distillation, vacuum distillation, fractional crystallization or solvent extraction.

7. A hydrogenated reaction product of the process which comprises
   a. heating a mixture of cyclopentadiene dimer and methylcyclopentadiene dimer at a temperature of 150°–250° C for from 10 minutes to 3 hours provided that any oxygen present will not exceed 0.1%w of the mixture, then
   b. hydrogenating the product of step (a) by reaction with sufficient hydrogen to completely saturate the olefinically unsaturated bonds of said product and in the presence of a hydrogenation catalyst at a temperature of from 25°–160° C and a hydrogen pressure of from 150–800 psig, which hydrogenated reaction product has a liquid density of about 1.029 gm/ml and melting point of about −30° C.

* * * * *